United States Patent
Norlin

(10) Patent No.: US 10,549,002 B2
(45) Date of Patent: Feb. 4, 2020

(54) METHOD FOR GUIDING A USER TO INTERVENE IN AN ON-GOING PROCESS IN A DEVICE FOR WASHING, DISINFECTING, DRYING AND/OR STERILIZING MEDICAL, DENTAL, LABORATORY AND/OR PHARMACEUTICAL GOODS

(71) Applicant: Getinge Sterilization AB, Gentige (SE)

(72) Inventor: Per Norlin, Torslanda (SE)

(73) Assignee: GETINGE STERILIZATION AB, Getinge (SE)

( * ) Notice: Subject to any disclaimer, the term of this patent is extended or adjusted under 35 U.S.C. 154(b) by 188 days.

(21) Appl. No.: 15/026,894

(22) PCT Filed: Oct. 3, 2013

(86) PCT No.: PCT/EP2013/070626
§ 371 (c)(1),
(2) Date: Apr. 1, 2016

(87) PCT Pub. No.: WO2015/049000
PCT Pub. Date: Apr. 9, 2015

(65) Prior Publication Data
US 2016/0220718 A1 Aug. 4, 2016

(51) Int. Cl.
*A61L 2/24* (2006.01)
*B08B 13/00* (2006.01)
(Continued)

(52) U.S. Cl.
CPC .................. *A61L 2/24* (2013.01); *B08B 3/04* (2013.01); *B08B 13/00* (2013.01); *F26B 9/06* (2013.01);
(Continued)

(58) Field of Classification Search
CPC .... A61L 2202/14; A61L 2202/24; A61L 2/24; B08B 13/00; B08B 3/04; F26B 25/00;
(Continued)

(56) References Cited

U.S. PATENT DOCUMENTS

| 2002/0085945 A1 | 7/2002 | Florkey et al. |
| 2005/0109070 A1* | 5/2005 | Kobayashi .............. D06F 33/02 68/3 R |
| 2006/0240563 A1* | 10/2006 | Kippenhan ............... A61L 2/24 436/100 |

FOREIGN PATENT DOCUMENTS

| CN | 1918567 A | 2/2007 |
| CN | 101082167 A | * 12/2007 |

(Continued)

OTHER PUBLICATIONS

Machine translation of CN101082167A (Year: 2007).*
(Continued)

*Primary Examiner* — Douglas Lee
(74) *Attorney, Agent, or Firm* — Aaron M. Miller

(57) ABSTRACT

Method and system for guiding a user to intervene in an on-going process in a device for washing, disinfecting, drying and/or sterilizing medical, dental, laboratory and/or pharmaceutical goods. The device includes a chamber for receiving the goods, a door, and a display. The device receives input from the user indicating an intention to intervene in the on-going process, optionally pauses the process, and displays a plurality of graphical interactive user-interface objects including a first object associated with aborting the process. If the process is considered resumable after a hypothetical opening of the door in the current process state, the objects include a second object associated with confirming holding the on-going process for subsequent resumption. Users may also cancel the intervention. Users are informed of consequences of intervening in the on-going process, and have control of how to proceed. The disclosure also relates to corresponding devices and computer programs.

23 Claims, 3 Drawing Sheets

(51) Int. Cl.
*F26B 9/06* (2006.01)
*F26B 25/00* (2006.01)
*G06F 3/0484* (2013.01)
*B08B 3/04* (2006.01)

(52) U.S. Cl.
CPC .......... *F26B 25/00* (2013.01); *G06F 3/04847* (2013.01); *A61L 2202/14* (2013.01); *A61L 2202/24* (2013.01)

(58) Field of Classification Search
CPC ........ F26B 9/06; G06F 3/04847; D06F 37/42; D06F 2224/00; A47L 2501/26
See application file for complete search history.

(56) References Cited

FOREIGN PATENT DOCUMENTS

| | | | |
|---|---|---|---|
| CN | 101214385 | A | 7/2008 |
| CN | 101219072 | A | 7/2008 |
| CN | 101605565 | A | 12/2009 |
| CN | 105473167 | A | 4/2016 |
| EP | 1882479 | A1 | 1/2008 |
| EP | 2340853 | A1 | 7/2011 |
| EP | 2340953 | A1 | 7/2011 |
| JP | H09-327503 | A | 12/1997 |
| JP | 2000-167030 | A | 6/2000 |
| JP | 3070060 | U | 7/2000 |
| JP | 2008-200126 | A | 9/2008 |
| WO | 8604698 | A1 | 8/1986 |
| WO | WO 8604698 A1 * | | 8/1986 ............... A61L 2/24 |
| WO | 2007021696 | A2 | 2/2007 |
| WO | WO-2012092445 A2 * | | 7/2012 ........... D06F 39/005 |

OTHER PUBLICATIONS

Operator Manual Basil 9500 Cage and Rack Washer dated Jan. 20, 2006 (Year: 2006).*
Tuttnauer Operation & Maintenance Manual Cat No. MAN205-0112003EN Rev. N (Year: 2011).*
Webpage printout from https://www.allclaveparts.com/tuttnauer-troubleshooting/tuttnauer-automatic-autoclaves/tuttnauer-autoclave-error-codes-display-messages as evidence for disclosing that the Tuttnauer autoclave available since at least 2011 (Year: 2011).*
International Search Report for Application No. PCT/EP2013/070626 dated Jan. 8, 2014.
Japanese Office Action (with English translation) issued during prosecution of corresponding Japanese Patent Application No. 2016-546146, dated Nov. 7, 2017 (5 pages).

* cited by examiner

METHOD FOR GUIDING A USER TO INTERVENE IN AN ON-GOING PROCESS IN A DEVICE FOR WASHING, DISINFECTING, DRYING AND/OR STERILIZING MEDICAL, DENTAL, LABORATORY AND/OR PHARMACEUTICAL GOODS

CROSS-REFERENCE TO RELATED APPLICATION

This application is a national phase entry under 35 U.S.C. § 371 of International Application No. PCT/EP 2013/070626, filed on Oct. 3, 2013, the disclosure of which is incorporated herein by reference.

TECHNICAL FIELD

The present disclosure relates to a device for washing, disinfecting, drying and/or sterilizing medical, dental, laboratory and/or pharmaceutical goods, and a method performed therein for guiding a user to intervene in an on-going process in said device.

BACKGROUND

The pharmaceutical industry, hospitals, care centers, laboratories and similar industries and facilities are constantly struggling against contaminations such as bacterial infections and viral infections which can spread. Hygiene issues are constantly on the topic and continuously evaluated. One hygiene issue of special character is the cleaning and sterilization of objects, such as reusable goods, disposable goods or other. For example, a pharmaceutical production site may be equipped with steam generators, water pretreatment apparatuses, closure processing systems, discharge systems, component washers, glassware washers, component sterilizers, terminal sterilization systems, isolators and sterility testing equipment, simply to clean and sterilize different reusable medical goods.

Reusable goods can be surgical equipment such as knifes, graspers, clamps, retractors, dialators, probes, scopes, drills, and saws, laboratory equipment such as bottles, bowls, condensers, funnels, flasks, pipettes, plates, media, cage fillings or the like. Any object which Is intended to be reused and which can be contaminated with hazardous or biological substances are the subject of harsh hygiene conditions. Whenever reusable goods has been used, such as reusable medical equipment, the reusable goods is sent for cleaning or sterilization.

The process of washing, disinfecting, drying and sterilizing reusable goods and/or disposable goods, such as reusable medical goods mentioned above, is a very high demanding process in terms of the facilities used, the staff, the process parameters, the apparatuses and even the ambient environment surrounding the apparatuses. All restrictions and conditions serving the purpose to reduce, or eliminate, the risk for contamination makes it difficult and costly to operate cleaning and sterilization processes.

Sterilization relates to a process that eliminates microbial life, including transmissible agents (such as fungi, bacteria, viruses, spore forms, etc.) present e.g. on or in a surface, contained in a fluid or powder, in medication, and/or on and/or in a compound such as biological culture media. Sterilization can be achieved by applying heat, chemicals, irradiation, high pressure, and filtration or combinations thereof.

Steam sterilization, or autoclaving, involves subjecting goods to steam at a high temperature. Steam sterilization involves the use of saturated steam under pressure and is a non-toxic method for sterilization. Further, steam sterilizers (autoclaves) are available in different sizes for different purposes. Four factors are relevant for the outcome of steam sterilization: steam, pressure, temperature and time. The sterilization time required varies depending on the goods to be sterilized. Chemical and biological indicators may be available for monitoring the sterilization process and to ensure that sterility is achieved. Properly executed steam sterilization will inactivate all fungi, bacteria, viruses and bacterial spores. If not all fungi, bacteria, viruses and bacterial spores can be removed or inactivated, the temperature, time and pressure is selected so that the sterilization device, and the method, has a Sterility assurance level, SAL, typically of at most 1/1.000.000, preferably lower than 1/1.000.000. SAL is used to describe the probability of a non-sterile unit exiting the device or method after the sterilization process has been completed.

Another example is high level disinfection (HLD), which is an accepted standard for the reprocessing of semi-critical devices, including flexible endoscopes, or for sterilization of critical or semi-critical devices that are heat-sensitive or incompatible with traditional sterilization methods. Endoscope reprocessing, for instance, involves the cleaning and disinfection of endoscopes, and may encompass the steps of cleaning, rinsing, disinfection, secondary rinsing, drying and storing. For drying, a drying cabinet is commonly utilized, which drying cabinet may comprise a door, a cabinet, a control circuit and a loading system such as one or several shelves or hooks. Use of the drying cabinet enables for immediate reuse of e.g. endoscopes, even after extended storage periods thereof.

During an on-going washing, disinfecting, drying and/or sterilizing process, an operator of the apparatus in which the process takes place, may be confronted with a need to prematurely stop the on-going process. A reason for intervening in the on-going process may for instance relate to an incorrect washing, disinfecting, drying and/or sterilizing program having been selected, a need to retrieve a loaded e.g. object or to add an object to the load, or having to adjust the placement of a load such as a bowl being turned upside-down. Unless the operator chooses to wait until the on-going process has been completed, which e.g. may take more than an hour, the operator commonly needs to activate an alarm in order to stop the on-going process. Activating an alarm may however be very stressful to the operator, who accordingly may feel disinclined to do so. Furthermore, choosing to stop the on-going process, e.g. by selecting a "Stop" button on a process screen associated with the apparatus and on-going process, may by the operator be perceived as a drastic measure, in that the act may be irrevocable. Additionally, the operator may not be knowledgeable of the impact on the load, should a door to the chamber containing the load be opened subsequent stopping the on-going process. The effect of the above is that the operator commonly chooses to avoid intervening in the on-going process, even though intervening in many cases would have been preferred.

SUMMARY OF THE INVENTION

It is therefore an object of embodiments herein to provide an improved way of guiding an operator of a device for washing, disinfecting, drying and/or sterilizing medical, dental, laboratory and/or pharmaceutical goods, to intervene in an on-going process of said device.

According to a first aspect of embodiments herein, the object is achieved by a method for guiding a user to intervene in an on-going process in a device for washing, disinfecting, drying and/or sterilizing medical, dental, laboratory and/or pharmaceutical goods. The device comprises a chamber for receiving the goods and at least one openable door associated with the chamber. The device further comprises at least one display. The method comprises receiving input from the user indicating an intention to intervene in the on-going process; pausing the on-going process in a current process state; and displaying, on the display, a plurality of selectable graphical interactive user-interface objects comprising a first object associated with confirming aborting the on-going process. If the on-going process is considered resumable subsequent a hypothetical opening of the at least one door in the current process state, the plurality of objects further comprises a second object associated with confirming holding the on-going process for a subsequent resumption thereof.

Thereby, by pausing the on-going process after acknowledging the user intending to intervene in the on-going process, and allowing the user to consider selectable options associated therewith, a solution is provided which enables the user to be informed of consequences of intervening in the on-going process and have control of how to proceed. For that reason, guiding an operator of a device for washing, disinfecting, drying and/or sterilizing medical, dental, laboratory and/or pharmaceutical goods, to intervene in an on-going process of said device, has been improved.

Another advantage is that, since the device takes into consideration whether the on-going process is considered resumable subsequent a hypothetical opening of the at least one door in the current process state, a solution is provided which enables for the device, rather than the operator, to judge whether opening of the door may result in not acceptable processing of the goods.

Yet another advantage is that the user may indicate an intention to intervene in the on-going process without the indication initially giving rise to an alarm status or having an impact on the on-going process. Accordingly, an approach is provided which enables the user to be more comfortable with interrupting the on-going process.

Another advantage is that, upon reception of user input indicating an intention to intervene in the on-going process, the on-going process is paused rather than automatically aborted, the latter commonly being the case in the art. Accordingly, the on-going process need not necessarily be re-run, i.e. re-started, after the user interruption, thus improving the throughput of the device.

Still another advantage is that the goods may be properly washed, disinfected, dried and/or sterilized in a controlled and secure manner even if the operator intervenes in the on-going process.

The technical features and corresponding advantages of the above mentioned method will be discussed in further detail in the following.

By introducing a method for guiding a user to intervene in an on-going process in a device for washing, disinfecting, drying and/or sterilizing medical, dental, laboratory and/or pharmaceutical goods, a user of such a device is assisted during the on-going process therein. The on-going process may be represented by e.g. a sterilizing program, such as a sterilizing program adapted for heavy goods, for light goods or for textiles. The process may further be considered to comprise pre-process stages, i.e. process start preparation stages, such as for instance pre-filling of water and/or heating of the chamber. Furthermore, the "user" may for instance be represented by an operator of the device. Medical, dental, laboratory and/or pharmaceutical goods is throughout this disclosure intended to relate to goods for, or used in, Bio-Pharmaceutical Production, Medical Device Production, Bio-Medical Research and Laboratories, Hospitals (Sterile processing departments & Wards), Outsourced sterilization, Clinics & Practice (i.e. Dentists) and/or Elderly care. The device for washing, disinfecting, drying and/or sterilizing medical, dental, laboratory and/or pharmaceutical goods using a washing, disinfecting, drying and/or sterilizing process, should preferably be adapted to operate at a temperature above 100° C., preferably above 120° C., more preferably between 120-140° C. and at suitable pressure, such as at least above 101.3 kPa. Should the device be a sterilizer, said sterilizer preferably meet the requirement of EN285:2006 and A2:2009, standards used in this field of technology and known to the skilled person in the art.

By the device comprising a chamber for receiving the goods and at least one openable door associated with the chamber, the device is adapted for washing, disinfecting, drying and/or sterilizing the goods in the chamber, and loading/unloading the goods through the at least one door. The at least one door may have any arbitrary shape suitable for the implementation at hand, and may for instance be represented by e.g. a flap or a lid. Should the device, for instance, be represented by an autoclave, there is commonly more than one door associated with the chamber. Furthermore, as well the chamber may have any arbitrary shape suitable for the implementation at hand, and may for instance be represented by e.g. a room, a container or a void.

By the device further comprising at least one display, the user may be presented with relevant information, and/or the ability to interact with the device via the display. "Display" is here intended to be interpreted in a broad manner, likewise including at least "screen".

The display may be a touch screen, which the user may control through simple, or e.g. multi-touch, gestures.

By receiving input from the user indicating an intention to intervene in the on-going process, the device acknowledges that the user has provided an indication of wanting to interfere with the on-going process. The input may for instance be provided from the user via the display, by the user e.g. selecting a graphical interactive user-interface object, such as a "cancel process button" or the like, which enables interfering with the on-going process. Alternatively and/or additionally, such input may be provided by means of voice recognition via a microphone associated with the device, and/or provided by means of actuation via a button, knob or keyboard associated with the device. "Intervene in" is throughout this disclosure intended to be interpreted to likewise include at least "interrupt", "interfere with" and "pause".

By pausing the on-going process in a current process state, the on-going process is taken to a temporary stop. That is, rather than instantly and/or automatically aborting the on-going process, the on-going process is merely paused in the current process state. Accordingly, the on-going process need not necessarily be re-started after the user interruption. Pausing the on-going process temporarily does not affect the process result. Furthermore, pausing the on-going process may occur essentially instantly upon reception of the input, or may occur with some time delay ranging up to several seconds, or even minutes, in order to, for instance, allow the on-going process to reach a suitable and/or preferred process state. The current process state may for instance be associated with a segment of an "in process" state. "Based on" is throughout this disclosure intended to be interpreted to likewise include at least "considering" and "taking into account".

By displaying, on the display, a plurality of selectable graphical interactive user-interface objects, there is provided the opportunity for the user to interact with the device, and subsequently the opportunity to control a next step of the device. The graphical interactive user-interface objects may for instance be represented by virtual buttons selectable via the display, as commonly known in the art. By the plurality of objects being "selectable", is here intended to emphasize that the objects indeed are possible to select by the user.

By the plurality of objects comprising a first object associated with confirming aborting the on-going process, there is provided an option for the user to select cancelling of the on-going process. Accordingly, the user is given the opportunity to confirm that he or she wishes to abort the on-going process. "Aborting the on-going process" may comprise restarting the on-going process from the beginning, after the user has intervened. Furthermore, the user may be informed of elapsed time and/or percentage of the on-going process. "Associated with confirming aborting" may for instance be represented by the on-going process being aborted, should the first object be selected. Furthermore, the first object may for instance be represented by a virtual button, comprising e.g. an explanatory text such as "Cancel program", "Abort program", or the like.

By taking into account if the on-going process is considered resumable subsequent a hypothetical opening of the at least one door in the current process state, consideration is taken to whether the paused on-going process may be resumed, should said door assumably be opened during the current process state. That is, opening the at least one door may result in unacceptable processing of the goods. Commonly, the operator is expected to be knowledgeable of whether or not the remaining part of the on-going process after resumption will result in the goods being properly processed at the end of the on-going process, which however may be difficult to judge. Accordingly, by the device taking into account whether the on-going process is considered resumable, there is no need for the operator to make such considerations. "Considered resumable" may for instance be associated with the goods being considered not to have been contaminated following opening of the at least one door. Furthermore, "hypothetical" opening of the door is here intended to refer to an "imagined" opening of the door, i.e. the door "assumably" being opened, rather than the door actually being opened.

By the plurality of objects in such a case further comprising a second object associated with confirming holding the on-going process for a subsequent resumption thereof, there is provided an option for the user to select a hold, e.g. a continued pausing, of the on-going process. Accordingly, the user is given the opportunity to confirm that he or she wishes to hold, rather than abort, the on-going process, for a subsequent resumption of the on-going process at a later point in time. Such a later point in time may for instance refer to the operator having closed the at least one door after having opened the door, e.g. for adjusting the goods. Thereby, the on-going process needs not necessarily be re-run after the user interruption, thus improving the throughput of the device. "Associated with confirming holding" may for instance be represented by the on-going process being put on hold, should the second object be selected. Furthermore, the second object may for instance be represented by a virtual button, comprising e.g. an explanatory text such as "Hold program", "Pause program", or the like.

According to an embodiment, the device may further determine whether the on-going process is resumable based on the current process state. Thereby, the current process state of the on-going process, in which pausing of the on-going process has occurred, may be taken into consideration when judging if the on-going process is considered resumable. The on-going process may for instance be "considered resumable" during one or several specific segments thereof, for instance during segments when opening of the door is considered to nonetheless result in acceptable processing of the goods at the end of the on-going process, in contrast to not being "considered resumable" during other segments, for instance during segments when opening of the door may result in not acceptable processing of the goods at the end of the on-going process. Conditions for judging whether or not a specific segment of the process is considered resumable may be predetermined.

According to another embodiment, the device may further determine that one object out of the plurality of objects has been selected by the user. The device may then further enable the on-going process to be aborted, if the selected object is the first object, and enable the on-going process to be on hold for a subsequent resumption thereof, if the selected object is the second object. Thereby, selection by the user of the first object may initiate an abort of the on-going process, while selection of the second object may initiate a hold, for a later resumption, of the on-going process. Accordingly, selection of the second object may enable for the on-going process to, in a safe manner, be resumed, without the risk of not having a proper processing of the goods. Selection of the first object may be appropriate should the operator have selected an incorrect process and hence wishes to change to another process, or should the option of the second object not be available. Selection of the second object may be appropriate if available, in that such a selection may enable for the on-going process to be resumed without the risk of the goods not being properly washed, disinfected, dried or sterilized at the end of the on-going process, rather than the on-going process being aborted and/or re-run.

Should neither of the first object or the potential second object be selected within a predetermined time frame, for instance within a few seconds or minutes, the device may enable the on-going process to be resumed without interaction by the user.

According to a further embodiment, the previously mentioned plurality of objects may further comprise a third object associated with denying the intention to interrupt the on-going process. The device may then further enable the on-going process to be resumed, if the selected object is the third object. Thereby, an option is provided the user to select essentially immediate resumption of the on-going process, i.e. without involving opening the at least one door. Accordingly, the user is given the opportunity to regret his or her indication of wishing to intervene in the on-going process. "Associated with denying the intention to interrupt" may for instance be represented by the on-going process being resumed, should the first object be selected. Furthermore, the first object may for instance be represented by a virtual button, comprising e.g. an explanatory text such as "Close", "X", or the like.

According to yet a further embodiment, if the selected object is the second object, the device may further enable the at least one door to be opened. Furthermore, the device may then enable the on-going process to be resumed, subsequent the previously mentioned enabling of the on-going process to be on hold, based on the at least one door being determined to have been closed. Thereby, the at least one door may be allowed to be opened so that the operator may manipulate the load, and subsequently, after the door has been acknowledged to be closed, the on-going process may be allowed to be resumed. Enabling the at least one door to be opened may for instance be represented by providing a graphical interactive user-interface object, which upon being selected, automatically opens the door or allows the user to open the door. The at least one door being determined to have been closed may for instance be based on input provided from one or several sensors, and/or as commonly determined in the art.

According to yet a further embodiment, the device may further be operated into a safe processing state prior to the previously mentioned enabling the at least one door to be opened. Thereby, the on-going process may, for instance, be continued until reaching a processing state considered to be safe, or be operated to return to a previous processing state considered to be safe. A safe processing state may for instance be represented by a preferred segment of the on-going process, which may be considered appropriate or convenient during hold of the on-going process. Additionally and/or alternatively, a safe processing state may for instance be represented by a preferred segment of the on-going process during which it may be considered non-hazardous for the user to open the at least one door. Additionally and/or alternatively, a safe processing state may for instance be represented by a preferred defined state during which it may be considered non-hazardous for the user to open the at least one door.

According to yet another embodiment, the previously mentioned enabling of the on-going process to be resumed, subsequent the previously mentioned enabling of the on-going process to be on hold, comprises enabling the on-going process to be resumed from the safe processing state. Thereby, the on-going process may be resumed from a state which may be considered preferred and/or appropriate.

According to a further embodiment, the device may further determine whether or not the goods has been sufficiently washed, disinfected, dried and/or sterilized. Furthermore, the device may then present, on the display, whether or not the goods has been sufficiently washed, disinfected, dried and/or sterilized. Thereby, the operator may be informed of the status of the washing, disinfecting, drying and/or sterilizing result. The device may further detect or confirm the current status of the process and display the current status of the process, such as at which stage the process is in, how much is left or the like.

According to another embodiment, the previously mentioned displaying a plurality of objects may comprise inactivating at least one unrelated graphical interactive user-interface object not associated with intervening in the on-going process. Thereby, unrelated objects may be suppressed, which unrelated objects prior to the user intervening were active on the display, but which after the user intervening, and subsequently after the on-going process has been paused, may be considered irrelevant, inapplicable, and/or unimportant to the user. That is, objects and/or information irrelevant to the user in the act of intervening in the on-going process may, for instance, be visualized in a suppressed manner, such as greyed, visualized with less intensity, or even not displayed at all. Thereby, the user is subjected to less options and/or information, and subsequently to a facilitated guiding of intervening in the on-going process. The unrelated object may for instance be represented by a virtual button.

According to an aspect, the method further comprises the step of denying the intention to intervene in the paused on-going process and optionally continuing with the on-going process.

According to a second aspect of embodiments herein, the object is achieved by a user of a device for washing, disinfecting, drying and/or sterilizing medical, dental, laboratory and/or pharmaceutical goods. The device comprises: a chamber for receiving the goods; at least one openable door associated with the chamber; at least one display; and processing circuitry. The processing circuitry is configured for: receiving input from the user indicating an intention to intervene in the on-going process; pausing the on-going process in a current process state; and displaying, on the display, a plurality of selectable graphical interactive user-interface objects comprising a first object associated with confirming aborting the on-going process. Furthermore, if the on-going process is considered resumable subsequent a hypothetical opening of the at least one door in the current process state, the plurality of objects further comprises a second object associated with confirming holding the on-going process for a subsequent resumption thereof.

According to an embodiment, the processing circuitry may further be configured for determining whether the on-going process is resumable based on the current process state.

According to a further embodiment, the processing circuitry may further be configured for determining that one object out of the plurality of objects has been selected by the user. The processing circuitry may then be configured for enabling the on-going process to be aborted, if the selected object is the first object, and enabling the on-going process to be on hold for a subsequent resumption thereof, if the selected object is the second object.

According to yet a further embodiment, the processing circuitry may further, if the selected object is the second object, be configured for: enabling the at least one door to be opened; and enabling the on-going process to be resumed, subsequent the previously mentioned enabling the on-going process to be on hold, based on the at least one door being determined to have been closed.

According to one embodiment, the device comprises an autoclave, a washer, a washer disinfector, or a drying cabinet for medical, dental, laboratory and/or pharmaceutical goods. Alternatively, said device may be represented by a device for any other sterilization method, such as e-beam radiation.

Similar advantages as those mentioned in the foregoing correspondingly apply to these embodiments of the second aspect, why these are not further discussed.

According to a third aspect of embodiments herein, the object is achieved by a computer program product for use in a device for washing, disinfecting, drying and/or sterilizing medical, dental, laboratory and/or pharmaceutical goods, which device comprises processing circuitry, a chamber for receiving the goods, at least one openable door associated with the chamber, and at least one display. The computer program product comprises code instructions configured for execution by the processing circuitry and which code instructions when executed in the device causes the device to: receive input from the user indicating an intention to intervene in the on-going process; pause the on-going process in a current process state; and display, on the display, a plurality of selectable graphical interactive user-interface objects comprising a first object associated with confirming aborting the on-going process, wherein, if the on-going process is considered resumable subsequent a hypothetical opening of the at least one door in the current process state, the plurality of objects further comprises a second object associated with confirming holding the on-going process for a subsequent resumption thereof.

Yet again, similar advantages as those mentioned in the foregoing correspondingly apply, why these are not further discussed.

It should be understood that said method of guiding a user to intervene in an on-going process in a device according to the foregoing, may require the display to be in an ON-state.

BRIEF DESCRIPTION OF THE DRAWINGS

The various aspects of the non-limiting embodiments of the invention, including particular features and advantages, will be readily understood from the following detailed description and the accompanying drawings, in which.

DETAILED DESCRIPTION

Figure 1:
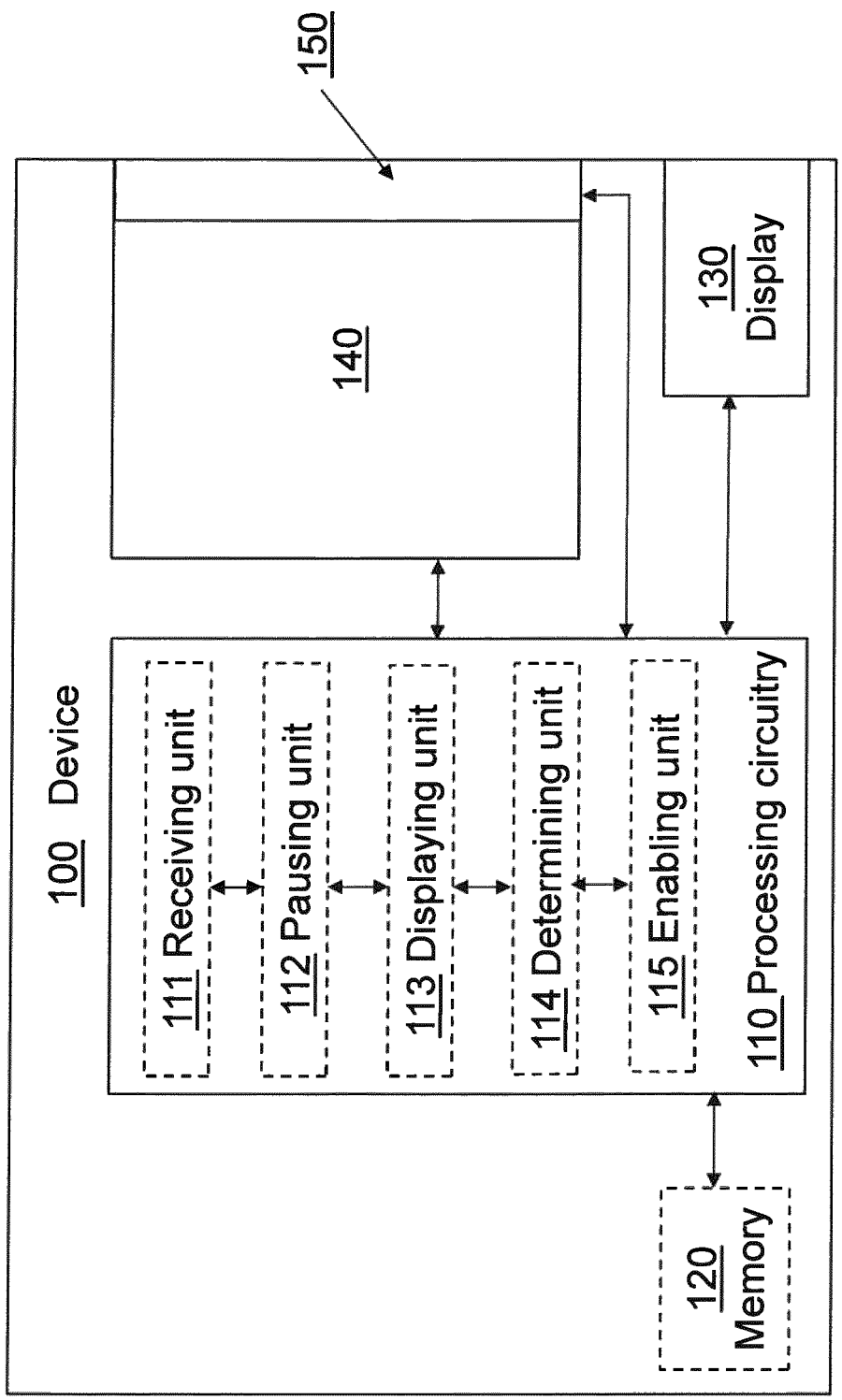
FIG. 1 a schematic block diagram illustrating an exemplifying device for washing, disinfecting, drying and/or sterilizing medical, dental, laboratory and/or pharmaceutical goods according to embodiments of the disclosure.

The non-limiting embodiments of the present disclosure will now be described more fully hereinafter with reference to the accompanying drawings, in which currently preferred embodiments of the disclosure are shown. This disclosure may, however, be embodied in many different forms and should not be construed as limited to the embodiments set forth herein. Like reference characters refer to like elements throughout. Dashed lines of some boxes in the figures indicate that these units or actions are optional and not mandatory.

In the following, according to embodiments herein which relate to guiding a user to intervene an on-going process in a device for washing, disinfecting, drying and/or sterilizing medical, dental, laboratory and/or pharmaceutical goods, there will be disclosed how an on-going process is paused after acknowledging a user's intention to intervene in the on-going process, how the user is allowed to consider selectable options associated therewith, and thus how the user is informed of consequences of intervening in the on-going process and have control of how to proceed.

Referring now to the figures and FIG. 1 in particular, there is depicted a schematic block diagram illustrating an exemplifying device 100 for washing, disinfecting, drying and/or sterilizing medical, dental, laboratory and/or pharmaceutical goods (not shown). The device 100 may according to embodiments herein comprise an autoclave, a washer, a washer disinfector, or a drying cabinet. The device 100 comprises a chamber 140 for receiving the goods, and at least one openable door 150 associated with the chamber 140. The device 100 furthermore comprises at least one display 130, which display 130 is a touch sensitive display.

Furthermore, the embodiments herein for guiding a user to intervene in an on-going process in a device for washing, disinfecting, drying and/or sterilizing medical, dental, laboratory and/or pharmaceutical goods 100 may be implemented through processing circuitry 110, together with computer program code for performing the functions and actions of the embodiments herein. Said program code may also be provided as a computer program product, for instance in the form of a data carrier carrying computer program code for performing the embodiments herein when being loaded into the device 100. One such carrier may be in the form of a CD ROM disc. It is however feasible with other data carriers such as a memory stick and/or other semiconductor memories. The computer program code may furthermore be provided as executable program code on a server and downloaded to the device 100. The device 100 may further comprise a memory 120 comprising one or more memory units. The memory 120 may be arranged to be used to store e.g. information, and further to store data and applications, to perform the methods herein when being executed in the device 100. The memory 120 and the processing circuitry 110 may for instance be implemented in one or several control units. The processing circuitry 110, which for instance may comprise a receiving unit 111, a pausing unit 112, a displaying unit 113, a determining unit 114 and an enabling unit 115, may refer to a combination of analog and digital circuits, and/or one or more processors configured with software and/or firmware, e.g. stored in a memory such as the memory 120, that when executed by the one or more processors perform as will be described in more detail later on in this description. One or more of these processors, as well as the other digital hardware, may be included in a single ASIC (Application-Specific Integrated Circuitry), or several processors and various digital hardware may be distributed among several separate components, whether individually packaged or assembled into a SoC (System-on-a-Chip).

Figure 2:
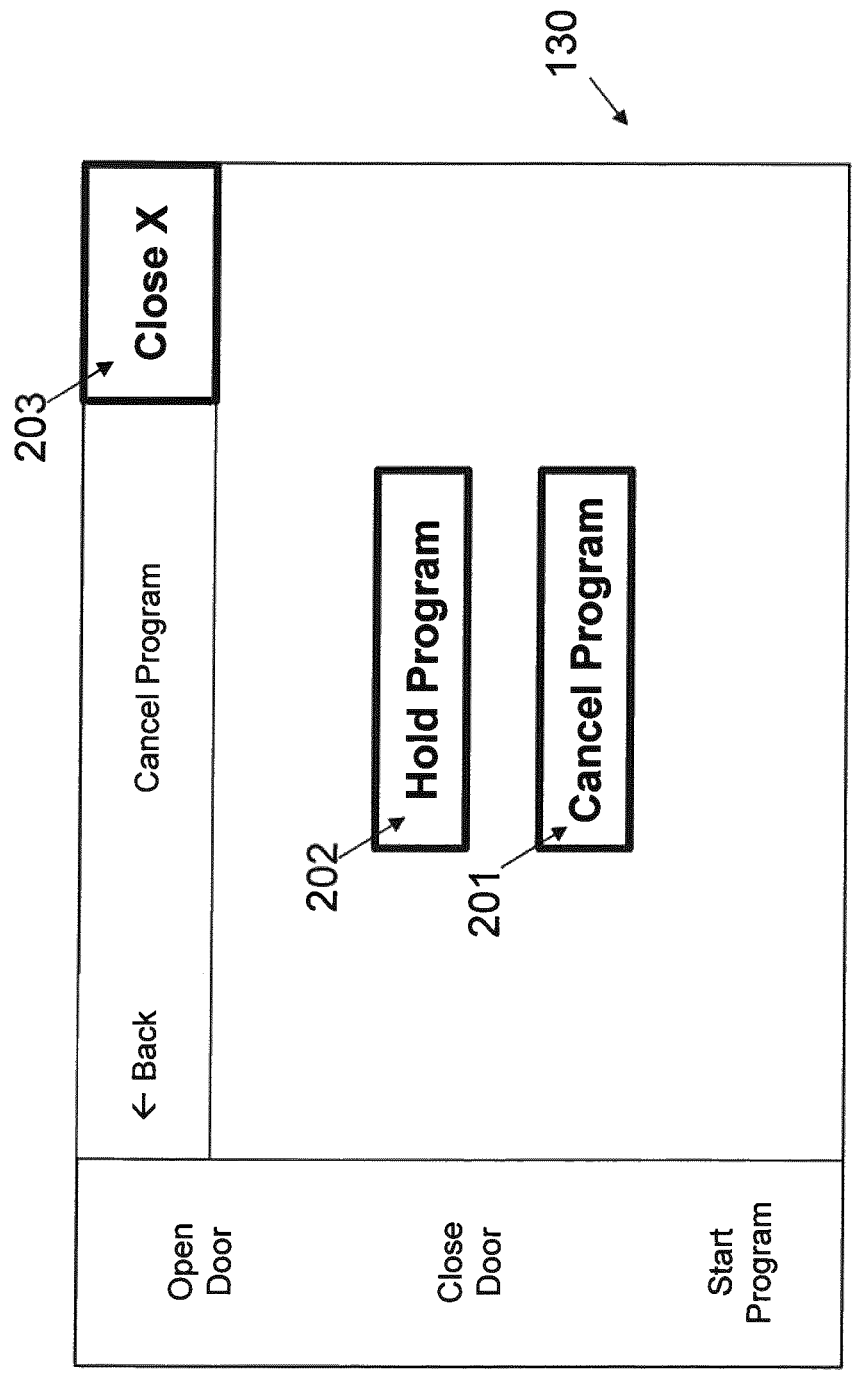
FIG. 2 shows an exemplifying display view comprising a plurality of selectable graphical interactive user-interface objects according to embodiments of the disclosure.

FIG. 2 shows an exemplifying display view of the display 130 comprising a plurality of selectable graphical interactive user-interface objects according to embodiments of the disclosure. Said display view has been preceded by the user indicating an intention to intervene in the on-going process.

The plurality of objects comprises a first object 201 associated with confirming aborting the on-going process, and potentially a second object 202 associated with confirming holding the on-going process for a subsequent resumption thereof. The subsequent resumption thereof can be a full restart of a sequence, or a partly restart of a sequence, e.g. keeping the washing water and just extending the exposure time (restarting the timer fully or partly). It can also be a direct resumption of the process from the hold position, or hold point, at which the process was put on hold.

According to embodiments herein, the plurality of objects may further comprise a third object 203 associated with denying the intention to intervene in the on-going process. As an option, preferably associated with the first object 201, an additional object could be representative for the stage in which the process is in or an object representative of the consequences if a user aborts the on-going process. With the first object 201 or the second object 202, it has been found that it is advantageous if a user is made aware of the consequences if aborting the on-going process. If a user can see that it will require a full restart of the entire process, the user might want to ignore to abort the on-going process and instead simply resume the process. Instead of an object representative for the stage in which the process is in or an object representative of the consequences if a user aborts the on-going process, the user can be presented with text describing the same.

The positioning, size, and layout of the plurality of objects 201, 202, 203 may be arbitrarily selected and adapted to the implementation at hand. Here, the first 301, the second 202 and the third 203 object are represented by virtual buttons, comprising explanatory text. Naturally, the plurality of objects 201, 202, 203 may additionally and/or alternatively comprise explanatory symbols. In order to distinguish the plurality of selectable objects 201, 202, 203 from other shown information, and from active or inactive graphical interactive user-interface objects unrelated with the plurality of objects resulting from the user indicating an intention to intervene in the on-going process, the plurality of objects 201, 202, 203 may be visualized e.g. with comparably larger and/or bolder fonts, and/or frames, different coloring, intensity, shadowing and the like.

Figure 3:
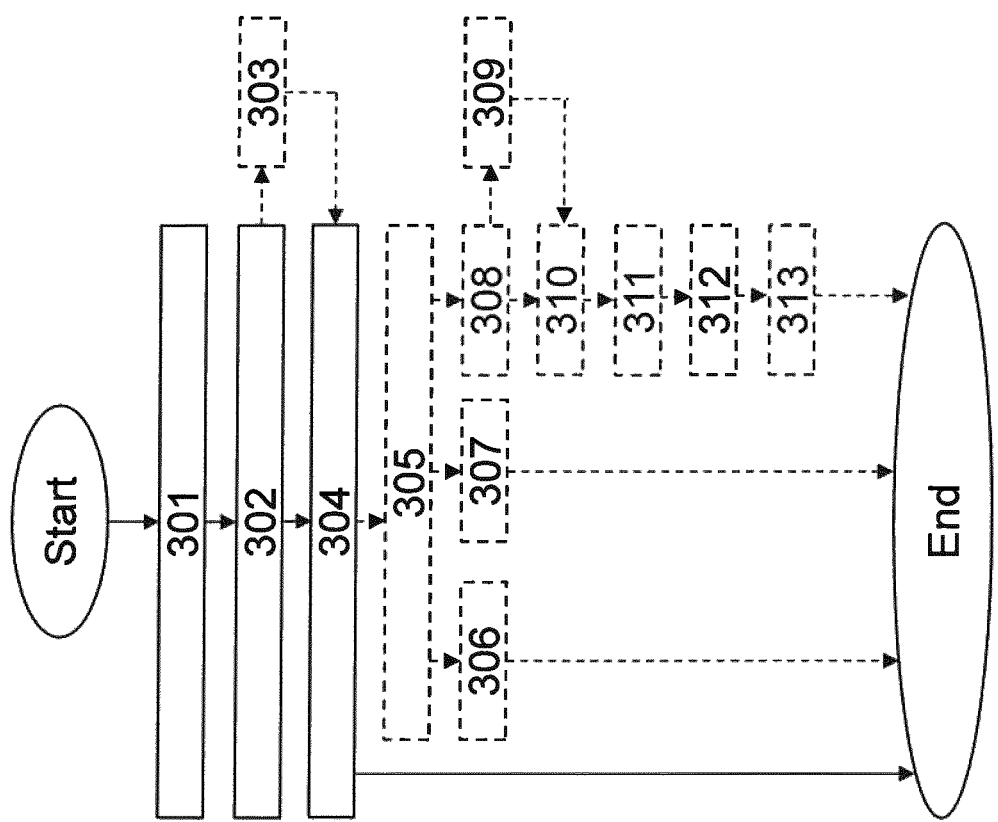
FIG. 3 is a flowchart depicting an exemplifying method for guiding a user to intervene in an on-going process in a device for washing, disinfecting, drying and/or sterilizing medical, dental, laboratory and/or pharmaceutical goods according to embodiments of the disclosure.

FIG. 3 is a flowchart depicting an exemplifying method for guiding a user to intervene in an on-going process in a device 100 for washing, disinfecting, drying and/or sterilizing medical, dental, laboratory and/or pharmaceutical goods, according to embodiments of the disclosure. The exemplifying method comprises the following actions discussed with support from FIGS. 1 and 2. The actions may be taken in any suitable order, and when applicable, taken in parallel.

Action 301

In Action 301, the device 100 receives, e.g. by means of the receiving unit 111, input from the user indicating an intention to intervene in the on-going process.

Action 302

In Action 302, the device 100 pauses, e.g. by means of the pausing unit 112, the on-going process in a current process state.

Action 303

In optional Action 303, the device 100 may determine, e.g. by means of the determining unit 114, whether the on-going process is resumable based on the current process state.

Action 304

In Action 304, the device 100 displays on the display 130, e.g. by means of the displaying unit 113, the plurality of selectable graphical interactive user-interface objects.

Action 305

In optional Action 305, the device 100 may determine, e.g. by means of the determining unit 114, that one object out of the plurality of objects 201, 202, 203 has been selected by the user.

Action 306

According to embodiments herein, the plurality of objects may further comprise the third object 203 associated with denying the intention to intervene in the on-going process. Consequently, in optional Action 306, the device may enable, e.g. by means of the enabling unit 115, the on-going process to be resumed. The resumption thereof can be a full restart of a sequence, or a partly restart of a sequence, e.g. keeping the washing water and just extending the exposure time (restarting the timer fully or partly). It can also be a direct resumption of the process from the hold position, or hold point, at which the process was put on hold.

Action 307

In optional Action 307, if the selected object is the first object 201, the device 100 may enable, e.g. by means of the enabling unit 115, the on-going process to be aborted.

Action 308

If the on-going process is considered resumable subsequent a hypothetical opening of the at least one door 150 in the current process state, the plurality of objects further comprises the second object 202 associated with confirming holding the on-going process for a subsequent resumption thereof. Consequently, in optional Action 308, if the selected object is the second object 202, the device 100 may enable, e.g. by means of the enabling unit 115, the on-going process to be on hold for a subsequent resumption thereof.

Action 309

In optional Action 309, subsequent the Action 308 of enabling the on-going process to be on hold, the device 100 may be operated, e.g. by means of the processing circuitry 110, into a safe processing state prior to enabling the at least one door 150 to be opened.

Action 310

In optional Action 310, if the selected object is the second object 202, the device 100 may enable, e.g. by means of the enabling unit 115, the at least one door 150 to be opened.

Action 311

In optional Action 311, subsequent the Action 310 of enabling the at least one door 150 to be opened, the device 100 may enable, e.g. by means of the enabling unit 115, the on-going process to be resumed, based on the at least one door 150 being determined to have been closed.

According to embodiments herein, should the device 100 have been operated into a safe processing state prior to enabling the at least one door 150 to be opened in accordance with Action 311, the on-going process may be resumed from the safe processing state.

Action 312

In optional Action 312, subsequent the Action 308 of enabling the on-going process to be on hold, the device 100 may determine, e.g. by means of the determining unit 114, whether or not the goods has been sufficiently washed, disinfected, dried and/or sterilized.

Action 313

In optional Action 313, the device 100 may present on the display 130, for instance by means of the processing circuitry 110, whether or not the goods has been sufficiently washed, disinfected, dried and/or sterilized.

Consequently, the solution as described in the foregoing thus allows an on-going process to be paused after learning of a user's intention to intervene in the on-going process, and further allows the user to consider selectable options associated therewith, in that the user is informed of consequences of intervening in the on-going process and have control of how to proceed. A user may for example initiate a full restart of a sequence, or a partly restart of a sequence, e.g. keeping the washing water and just extending the exposure time (restarting the timer fully or partly). The user can also be initiate a direct resumption of the process from the hold position, or hold point, at which the process was put on hold.

The person skilled in the art realizes that the present disclosure by no means is limited to the preferred embodiments described above. On the contrary, many modifications and variations are possible within the scope of the appended claims. It should furthermore be noted that the drawings not necessarily are to scale and the dimensions of certain features may have been exaggerated for the sake of clarity. Emphasis is instead placed upon illustrating the principle of the embodiments herein. Additionally, in the claims, the word "comprising" does not exclude other elements or steps, and the indefinite article "a" or "an" does not exclude a plurality.

The invention claimed is:

1. A device for washing, disinfecting, drying and/or sterilizing medical, dental, laboratory and/or pharmaceutical goods, which device comprises:

a chamber for receiving said goods;
at least one door associated with said chamber;
at least one display; and
processing circuitry;
the device and the processing circuitry being configured for:
receiving input from said user indicating an intention to intervene in an on-going process and, in response, and with said at least one door in a locked state:
determining whether said ongoing process would be resumable subsequent a hypothetical opening of said at least one door in a current process state, the determining including determining whether a remaining part of the ongoing process is sufficient to result in the goods being adequately processed;
displaying, on said display, a plurality of objects, the plurality of objects being selectable graphical interactive user-interface objects comprising a first object associated with confirming aborting the on-going process;
in response to determining that said on-going process would be resumable subsequent said hypothetical opening of the at least one door in the current process state, including determining that the remaining part of the ongoing process is sufficient to result in the goods being adequately processed: displaying a second object configured for confirming holding the on-going process for a subsequent resumption thereof, and also configured for enabling opening of the at least one door; and
in response to a determination that the remaining part of the on-going process is not sufficient to result in the goods being adequately processed, to not display the second object.

2. The device in accordance with claim 1, wherein said processing circuitry further is configured for:
determining that one object out of said plurality of objects has been selected by said user; and
aborting said on-going process if said first object is selected, and putting said on-going process on hold for subsequent resumption if said second object is selected.

3. The device in accordance with claim 1, wherein said device comprises an autoclave, a washer, a washer disinfector, or a drying cabinet.

4. The device in accordance with claim 1, the device being further configured wherein:
the at least one display comprises a touch-sensitive screen;
said input from the user indicating an intention to intervene in the on-going process is receivable by a user interaction with the touch-sensitive screen;
said displaying of the first object and, when present, of the second object, is on the touch-sensitive screen;
the device being configured to change the at least one door from a non-openable state to an openable state in response to a user interaction with the second object on the touch-sensitive screen when the second object is present.

5. The device in accordance with claim 1:
wherein predetermined conditions for determining whether a process is resumable, based on the current process state, are accessible by the device;
wherein the processing circuitry is configured to determine if the process is resumable subsequent said hypothetical opening of said at least one door in the current process state, by comparing the current process state to the predetermined conditions, in response to input from said user indicating an intention to intervene in said on-going process.

6. The device in accordance with claim 1, the device being further configured wherein:
the at least one display comprises a touch-sensitive screen;
wherein a third object is associated with denying said intention to intervene in said on-going process, after the intention to intervene has been indicated;
wherein the displaying includes displaying the first object, the third object, and when present, of the second object, on the touch-sensitive screen; and
wherein the device is configured to resume the paused on-going process in said current process state when a user interacts with the third object on the touch-sensitive screen.

7. The device in accordance with claim 1, the device and the processing circuitry being further configured to pause said on-going process in the current process state in response to said receiving input from said user indicating an intention to intervene in the on-going process.

8. The device in accordance with claim 1, the device and the processing circuitry being further configured wherein said receiving input from said user indicating an intention to intervene in the on-going process does not impact the ongoing process.

9. A device for washing, disinfecting, drying and/or sterilizing medical, dental, laboratory and/or pharmaceutical goods, which device comprises:
a chamber for receiving said goods;
at least one door associated with said chamber;
at least one display, the at least one display comprising a touch-sensitive screen; and
processing circuitry;
the device and the processing circuitry being configured for:
receiving input from said user indicating an intention to intervene in said an on-going process via the touch-sensitive screen and, in response, and with said at least one door in a locked state:
determining whether said ongoing process would be resumable subsequent a hypothetical opening of said at least one door in a current process state;
displaying, on said touch-sensitive screen, a plurality of objects, the plurality of objects being selectable graphical interactive user-interface objects comprising a first object associated with confirming aborting the on-going process, and
in response to determining that said on-going process would be resumable subsequent said hypothetical opening of the at least one door in the current process state, displaying a second object on the touch-sensitive screen configured for confirming holding the on-going process for a subsequent resumption thereof, and also configured for enabling opening of the at least one door in response to a user interaction with the second object on the touch-sensitive screen;
wherein the device comprises an autoclave, a washer, a washer disinfector, or a drying cabinet.

10. The device in accordance with claim 9, wherein said processing circuitry further is configured for determining whether said on-going process is resumable subsequent said hypothetical opening of the at least one door based on said current process state, the current process state being an operating state in an on-going washing, disinfecting, drying, or sterilizing process.

11. The device in accordance with claim 9, wherein said processing circuitry, if said selected object is said second object, further is configured for:
  enabling said on-going process to be on hold for a subsequent resumption thereof, if said selected object is said second object;
  enabling said at least one door to be opened; and
  enabling said on-going process to be resumed, based on said at least one door being determined to have been closed.

12. The device in accordance with claim 9, the device and the processing circuitry being further configured:
  wherein the plurality of objects comprises a third object associated with denying said intention to intervene in said on-going process after the intention to intervene has been indicated; and
  wherein when a user selects the third object the on-going process is continued without interruption.

13. A device for washing, disinfecting, drying and/or sterilizing medical, dental, laboratory and/or pharmaceutical goods, which device comprises:
  a chamber for receiving said goods;
  at least one door associated with said chamber;
  at least one display; and
  processing circuitry;
  the device and the processing circuitry being configured for:
  receiving input from said user indicating an intention to intervene in an on-going process and, in response, and with said at least one door in a locked state:
    determining whether said ongoing process would be resumable subsequent a hypothetical opening of said at least one door based on a current process state, the current process state being an operating state in an on-going washing, disinfecting, drying, or sterilizing process;
    displaying, on said display, a plurality of objects, the plurality of objects being selectable graphical interactive user-interface objects optionally comprising a first object associated with confirming aborting the on-going process, and
    in response to determining that said on-going process would be resumable subsequent said hypothetical opening of the at least one door in the current process state, displaying a second object configured for confirming holding the on-going process for a subsequent resumption thereof, and also configured for enabling opening of the at least one door.

14. The device in accordance with claim 13, the device and the processing circuitry being further configured to not display the second object in response to determining that said on-going process would not be resumable subsequent said hypothetical opening of the at least one door in the current process state.

15. The device according to claim 13:
  wherein the plurality of objects comprises a third object associated with denying said intention to intervene in said on-going process after the intention to intervene has been indicated;
  the device being configured wherein when a user selects the third object, the on-going process is continued without interruption.

16. The device according to claim 13:
  wherein the processing circuitry is configured for receiving input from the user, for said determining whether the ongoing process would be resumable subsequent a hypothetical opening of said at least one door, and for causing said displaying of the plurality of objects on the display.

17. A method for guiding a user to intervene in an on-going process in a device for washing, disinfecting, drying and/or sterilizing medical, dental, laboratory and/or pharmaceutical goods, said method comprising:
  providing a device according to claim 13;
  receiving input from said user indicating an intention to intervene in said on-going process and, in response, and with said as least one door in a locked state:
    determining whether said ongoing process would be resumable subsequent a hypothetical opening of said at least one door in a current process state;
    displaying, on said display, a plurality of objects, the plurality of objects being selectable graphical interactive user-interface objects comprising a first object associated with confirming aborting said on-going process, and
    in response to determining that said on-going process would be resumable subsequent said hypothetical opening of the at least one door in the current process state, displaying a second object configured for confirming holding the on-going process for a subsequent resumption thereof, and also configured for enabling opening of the at least one door.

18. The method in accordance with claim 17, wherein said method further comprises:
  determining whether said on-going process is resumable based on said current process state.

19. The method in accordance with claim 17, wherein said method further comprises:
  determining that the second object has been selected by said user; and
  holding said on-going process for a subsequent resumption thereof in response to the second object being selected.

20. The method in accordance with claim 19, wherein said plurality of objects further comprises a third object associated with denying said intention to intervene in said on-going process, said method further comprising:
  displaying the third object, and resuming the on-going process in response to the third object being selected.

21. The method in accordance with claim 19, wherein said method further comprises:
  enabling said at least one door to be opened in response to the second object being selected; and
  subsequently enabling said on-going process to be resumed, based on said at least one door being determined to have been closed.

22. The method in accordance with claim 21, wherein said method further comprises:
  operating said device into a safe processing state prior to said enabling the at least one door to be opened.

23. The method in accordance with claim 17, wherein said displaying the plurality of objects comprises inactivating at least one unrelated graphical interactive user-interface object not associated with intervening in the on-going process.

* * * * *